(12) United States Patent
Gestwicki et al.

(10) Patent No.: US 9,675,623 B2
(45) Date of Patent: Jun. 13, 2017

(54) NON-SURGICAL METHOD OF TREATMENT FOR CATARACT

(71) Applicant: THE REGENTS OF THE UNIVERSITY OF MICHIGAN, Ann Arbor, MI (US)

(72) Inventors: Jason E. Gestwicki, Moss Beach, CA (US); Kathryn McMenimen, South Hadley, MA (US); Leah Makley, San Francisco, CA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 13/944,477

(22) Filed: Jul. 17, 2013

(65) Prior Publication Data

US 2014/0031327 A1     Jan. 30, 2014

Related U.S. Application Data

(60) Provisional application No. 61/672,569, filed on Jul. 17, 2012.

(51) Int. Cl.

| | | |
|---|---|---|
| *A61K 31/56* | (2006.01) | |
| *A61K 31/575* | (2006.01) | |
| *A61K 47/48* | (2006.01) | |
| *A61K 31/045* | (2006.01) | |
| *G01N 33/68* | (2006.01) | |
| *C07J 9/00* | (2006.01) | |
| *C12Q 1/34* | (2006.01) | |
| *B82Y 5/00* | (2011.01) | |
| *A61K 9/00* | (2006.01) | |
| *G01N 21/64* | (2006.01) | |

(52) U.S. Cl.
CPC .......... *A61K 31/575* (2013.01); *A61K 9/0048* (2013.01); *A61K 31/045* (2013.01); *A61K 47/48969* (2013.01); *B82Y 5/00* (2013.01); *C07J 9/00* (2013.01); *C12Q 1/34* (2013.01); *G01N 21/6428* (2013.01); *G01N 33/68* (2013.01); *G01N 2201/10* (2013.01); *G01N 2333/4709* (2013.01); *G01N 2500/20* (2013.01)

(58) Field of Classification Search
None
See application file for complete search history.

(56) References Cited

U.S. PATENT DOCUMENTS

| | | | | |
|---|---|---|---|---|
| 2002/0132758 A1* | 9/2002 | Shell | | 514/2 |
| 2003/0229062 A1 | 12/2003 | Schwartz et al. | | |
| 2004/0019027 A1 | 1/2004 | Forman et al. | | |
| 2004/0204409 A1 | 10/2004 | Ando et al. | | |
| 2010/0112030 A1* | 5/2010 | Parhami et al. | | 424/423 |
| 2011/0033468 A1 | 2/2011 | Shih et al. | | |

FOREIGN PATENT DOCUMENTS

| | | | |
|---|---|---|---|
| WO | WO 03049685 A2 * | 6/2003 | |
| WO | WO-2010109212 A2 | 9/2010 | |

OTHER PUBLICATIONS

Sacconi et al., "A novel CRYAB mutation resulting in multisystemic disease," Neuromuscular Disorders 22 (2012) 66-72 (published online Sep. 22, 2011).*
Loftsson et al., "Cyclodextrins in eye drop formulations: enhanced topical delivery of corticosteroids to the eye," Acta Ophthalmol Scand. Apr. 2002;80(2):144-50 (Abstract).*
Osada et al., "Oxidation of Cholesterol by Heating," J. Agric. Food Chem. 1993, 41, 1198-1202.*
Brown and Jessup Atherosclerosis 1999; 142:1-28.*
Andley et al., A knock-in mouse model for the R120G mutation of αB-crystallin recapitulates human hereditary myopathy and cataracts. *PLoS One*, 6(3):e17671 (2011).
Bloemendal et al., Ageing and vision: structure, stability and function of lens crystallins. *Prog Biophys. Mol. Biol.*, 86(3):407-85 (2004).
Cummings et al., Universal Screening Methods and Applications of ThermoFluor. *J. Biomol. Screen*, 11:854 (2006).
Garbuzova-Davis et al., Blood-Brain Barrier Impairment in an Animal Model of MPS III B. *PLoS One*, 6:3, 1-13 (2011).
Garty et al., Sustained antibiotic release from an intraocular lens-hydrogel assembly for cataract surgery. *Invest Ophthalmol. Vis. Sci.*, 52(9):6109-16 (2011).
Gwon et al., Ophthalmic rods. New ocular drug delivery devices. *Ophthalmology*, 93(9 Suppl):82-5 (1986).
Haslbeck et al., Some like it hot: the structure and function of small heat-shock proteins. *Nat. Struct. Mol. Biol.*, 12:842-46 (2005).
Meehan et al., Amyloid fibril formation by lens crystallin proteins and its implications for cataract formation. *J. Biol. Chem.*, 279(5):3413-9 (2004).
Meehan et al., Characterisation of amyloid fibril formation by small heat-shock chaperone proteins human alphaA-, alphaB- and R120G alphaB-crystallins. *J. Mol. Biol.*, 372(2), 470-84 (2007).
Perng et al., The cardiomyopathy and lens cataract mutation in alphaB-crystallin alters its protein structure, chaperone activity, and interaction with intermediate filaments in vitro. *J. Biol. Chem.*, 274(47):33235-43 (1999).

(Continued)

*Primary Examiner* — Jared D Barsky
(74) *Attorney, Agent, or Firm* — Marshall, Gerstein & Borun LLP

(57) ABSTRACT

The invention provides inhibitors of α-crystallin aggregation and methods of using α-crystallin aggregation inhibitors to, e.g., treat or prevent cataracts in a subject having or at risk of developing cataracts. The invention further provides high throughput methods of screening compounds for modulation of protein thermal stability, the method comprising contacting a protein with each of a plurality of test compounds; and (b) measuring the melting transition ($T_m$) of the protein in the presence of each of the plurality of test compounds, wherein a compound that decreases or increases the apparent $T_m$ by at least 2 standard deviations is identified as a pharmacological protein chaperone.

1 Claim, No Drawings

(56) References Cited

OTHER PUBLICATIONS

Sloan, K. B., *Prodrugs*, M. Dekker, New York, (1992).
Testa et al., Hydrolysis in drug and prodrug metabolism: chemistry, biochemistry, and enzymology, Wiley-VCH, Zurich, (2003).
Vicart et al., A missense mutation in the B-crystallin chaperone gene causes a desmin-related myopathy, *Nat. Genet.*, 20(1):92-5 (1998).
Wagh et al., Polymers used in ocular dosage form and drug delivery systems. *Asian J. Pharm.*, 2(1):12-17 (2008).
International Search Report and Written Opinion for Application No. PCT/US2013/050866, dated Jan. 22, 2014.
International Preliminary Report on Patentability, PCT/US2013/050866, dated Jan. 20, 2015.
Liu, et al. A novel alphaB-crystallin mutation associated with autosomal dominant congenital lamellar cataract. Invest Ophthalmol Vis Sci. Mar. 2006;47(3):1069-75.
Song, et al. Cholesterol-derived bile acids enhance the chaperone activity of α-crystallins. Cell Stress Chaperones. Sep. 2011;16(5):475-80. doi: 10.1007/s12192-011-0259-5. Epub Mar. 6, 2011.
Yokoyama, et al. Anti-tumor effects of 25-hydroxycholesterol and low-dose recombinant tumor necrosis factor-alpha on rat liver tumorigenesis: modulated differentiation therapy for hepatocellular carcinoma. Int J Oncol. May 2000;16(5):1029-33.

\* cited by examiner

NON-SURGICAL METHOD OF TREATMENT FOR CATARACT

CROSS REFERENCE TO RELATED APPLICATIONS

This application claims priority to U.S. Provisional Patent Application No. 61/672,569, filed Jul. 17, 2012, which is hereby incorporated by reference in its entirety.

STATEMENT OF GOVERNMENT INTEREST

This invention was made with government support under RR024986 awarded by the National Institutes of Health. The government has certain rights in the invention.

FIELD OF THE INVENTION

The disclosure generally relates to inhibitors of α-crystallin aggregation, uses thereof, and methods of screening for therapeutically effective modulators of protein aggregation.

BACKGROUND OF THE INVENTION

Cataract, or a clouding of the eye lens, is a condition affecting over half of all adults over the age of 80, with approximately 25 million patients suffering from the condition in the United States. Moreover, cataracts are thought to be the leading cause of blindness worldwide. αA-crystallin (cryAA) and αB-crystallin (cryAB) comprise thirty percent of the protein content of the eye lens, where they are responsible for maintaining lens transparency (Haslbeck et al., *Nat Struct Mol Biol* 12, 842 (2005). cryAA and cryAB belong to a family of small heat shock proteins (sHSPs) that contain a conserved crystallin domain (Bloemendal et al., *Prog Biophys Mol Biol* 86, 407 (2004); Haslbeck, supra). Once synthesized, these lens sHSPs are never degraded, so any damage accumulates through life and eventually leads to aging-associated cataract (Haslbeck, supra; Perng et al., *J Biol Chem* 274, 33235 (1999); Meehan et al., *J Biol Chem* 279, 3413 (2004); Meehan et al., *J Mol Biol* 372, 470 (2007)). Similarly, destabilizing mutations in cryAB, such as R120G, result in hereditary forms of cataract with early onset (Vicart et al., *Nat Genet.* 20, 92 (1998)). In hereditary cataract, cryAB is prone to aggregation and forms amyloid-like fibrils in vitro (Andley et al., *PLoS One* 6, e17671 (2011)).

Currently, treatment for cataracts includes surgery to excise the clouded lens and insert an artificial replacement. Surgery can be costly and is not appropriate for all patients. Therapies which target the underlying mechanism of protein aggregation would benefit these patients. Thus, there remains a need in the art for therapeutics and methods of screening for therapeutics that block aggregation-prone proteins, such as cryAB, from forming pathological aggregates (e.g., aggregates associated with cataracts).

SUMMARY OF THE INVENTION

The invention provides a method of treating or preventing cataract, the method comprising administering to an individual in need thereof an effective amount of a composition comprising a compound of formula I:

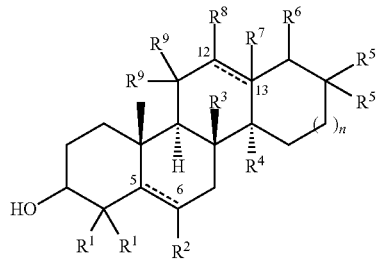

wherein:

both $R^1$ are H or both $R^1$ are Me;

$R^2$ is H or OH;

dashed line between carbons 5 and 6 indicates an optional double bond;

$R^3$ is H or Me;

$R^4$ is H or Me;

n is 0 or 1;

(a) $R^6$ is

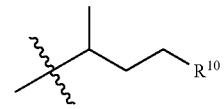

and each $R^5$ is independently H or Me or (b) $R^6$ and one $R^5$ taken together form an optionally substituted 6-membered ring and the other $R^5$ is Me;

the dashed line between carbons 12 and 13 is an optional double bond, with the proviso that $R^7$ is not present when the double bond between carbons 12 and 13 is present, and $R^7$ is H or Me when the double bond between carbons 12 and 13 is not present;

$R^8$ is H or OH;

both $R^9$ together form an oxo (=O) or both $R^9$ are hydrogen; and $R^{10}$ is $CO_2H$ or linear or branched $C_1$-$C_6$ alkyl;

or a prodrug or pharmaceutically acceptable salt thereof.

The invention also provides an ophthalmic pharmaceutical composition comprising a pharmaceutically acceptable ophthalmic carrier and a compound of formula I.

In various aspects of the method and/or composition, the compound of formula I has a structure of formula IA or formula IB:

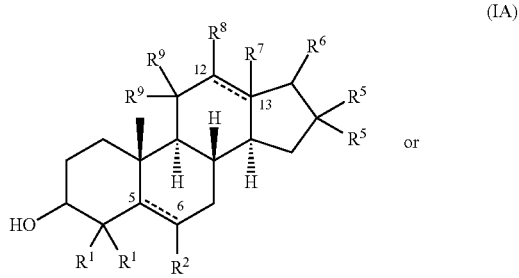

-continued

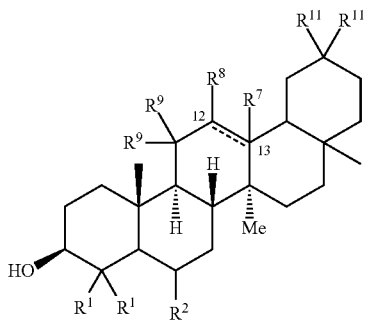

(IB)

wherein each $R^{11}$ is independently alkyl, $CO_2H$, or $CO_2$alkyl.

In a more specific aspect of the method and/or composition, the compound has a structure of formula II:

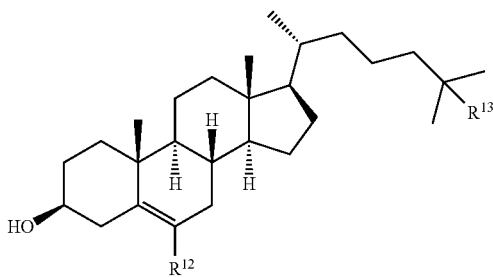

(II)

wherein $R^{12}$ is H or OH and $R^{13}$ is H or OH. In one aspect of the method and/or composition, the compound is 5-cholestin-3b,25-diol.

In various aspects of the method, the composition is administered topically, subconjunctivally, retrobulbarly, periocularly, subretinally, suprachoroidally, or intraocularly. In various aspects of the method, the cataract is an age-related cataract or a diabetic cataract. In some aspects of the method, the individual has a hereditary form of cataract with early onset. In more specific aspects of the method, the individual has a R120G mutation and/or a D109H mutation in cryAB.

In some aspects of the composition, the pharmaceutically acceptable ophthalmic carrier is a cyclodextrin. In a specific aspect, the cyclodextrin is (2-hydroxypropyl)-β-cyclodextrin.

Additionally, the invention includes a high-throughput method of screening compounds for modulation of protein thermal stability, the method comprising: (a) contacting a protein with each of a plurality of test compounds; and (b) measuring the melting transition ($T_m$) of the protein in the presence of each of the plurality of test compounds, wherein a compound that decreases or increases the apparent $T_m$ by at least 2 standard deviations is a pharmacological protein chaperone.

In various aspects of the method, the protein is an amyloid-forming protein or a protein underlying a loss-of-function disease. In some aspects, the amyloid-forming protein is selected from the group consisting of Hsp27, αA-crystallin, αB-crystallin, βB2-crystallin, βB1-crystallin, γD-crystallin, Hsp22, Hsp20, tau, Alpha-synuclein, IAPP, beta-amyloid, PrP, Huntingtin, Calcitonin, Atrial natriuretic factor, Apolipoprotein AI, Serum amyloid A, Medin, Prolactin, Transthyretin, Lysozyme, Beta 2 microglobulin, Gelsolin, Keratoepithelin, Cystatin, Immunoglobulin light chain AL, and S-IBM. In other aspects, the protein underlying a loss-of-function disease is selected from the group consisting of mutant β-glucosidase, cystic fibrosis transmembrane receptor, hexosaminidase A, hexosaminidase B, β-galactosidase, and alpha-glucosidase.

In some aspects of the method, the $T_m$ is determined using a high-throughput differential scanning fluorimetry device.

In one aspect of the method, the measuring step comprises: (b1) heating the protein in the presence of each of a plurality of test compounds from 50° C. to 80° C., (b2) cooling the protein to 25° C., (b3) maintaining the protein at 25° C. for 10 seconds, and (b4) measuring the fluorescence of the protein.

In various aspects, the method further comprises repeating steps (b1)-(b4) between 2 and 30 times, wherein each repeat of step (b1) is performed at an incrementally higher temperature. In specific aspects, the amyloid-forming protein is heated from 65° C. to 80° C. in 1° C. increments. In other aspects, (b1) further comprises, after heating, equilibrating the amyloid-forming protein and test compound between 60 and 180 seconds. In various aspects of the method, the equilibrating step is 130 seconds.

Additionally, the invention includes a high-throughput screening system, comprising: (a) an amyloid-forming protein; (b) a device capable of measuring the melting transition ($T_m$) of the amyloid-forming protein; and (c) a plurality of test compounds.

In various aspects of the screening system, the protein is selected from the group consisting of Hsp27, αA-crystallin, αB-crystallin, βB2-crystallin, βB1-crystallin, γD-crystallin, Hsp22, Hsp20, tau, Alpha-synuclein, IAPP, beta-amyloid, PrP, Huntingtin, Calcitonin, Atrial natriuretic factor, Apolipoprotein AI, Serum amyloid A, Medin, Prolactin, Transthyretin, Lysozyme, Beta 2 microglobulin, Gelsolin, Keratoepithelin, Cystatin, Immunoglobulin light chain AL, and S-IBM.

In some aspects of the screening system, the device is a high-throughput differential scanning fluorimetry device.

The use of the compound of any one of structural formulas I, IA, IB, or II in any of the methods disclosed herein or for preparation of medicaments for administration according to any of the methods disclosed herein is specifically contemplated. In this regard, the invention provides a compound of any one of structural formulas I, IA, IB, or II for use in a method of treating or preventing cataract, wherein the method comprises administering to an individual in need thereof an effective amount the compound.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description. The entire document is intended to be related as a unified disclosure, and it should be understood that all combinations of features described herein are contemplated, even if the combination of features are not found together in the same sentence, or paragraph, or section of this document. In addition to the foregoing, the invention includes, as an additional aspect, all embodiments of the invention narrower in scope in any way than the variations specifically mentioned above. For example, if aspects of the invention are described as "comprising" a feature, embodiments also are contemplated "consisting of" or "consisting essentially of" the feature.

DETAILED DESCRIPTION OF THE INVENTION

The invention provides inhibitors of α-crystallin aggregation and methods of using α-crystallin aggregation inhibitors to, e.g., treat or prevent cataracts in a subject having or at risk of developing cataracts. Inhibitors of α-crystallin aggregation of the invention are, e.g, sterols represented by Formula I, Formula IA, Formula IB, and Formula II and may be formulated in ophthalmic pharmaceutical compositions comprising a pharmaceutically acceptable ophthalmic carrier. Because cataracts affect such a large portion of the population (over half of all adults over the age of 80) and the predominant treatment is surgical intervention, the discoveries described herein represent a significant advancement in the non-surgical methodologies available for treating cataracts. Moreover, many non-surgical treatments currently in use tend to inhibit further aggregation of α-crystallin. Remarkably, compounds of the invention are able to reverse aggregation of α-crystallin and inhibit further aggregation of α-crystallin.

The invention further provides high-throughput methods of screening compounds for modulation of protein thermal stability, the method comprising contacting a protein with each of a plurality of test compounds; and measuring the melting transition ($T_m$) of the protein in the presence of each of the plurality of test compounds, wherein a compound that decreases or increases the apparent $T_m$ by at least 2 standard deviations is identified as a pharmacological protein chaperone.

Methods of Treating or Preventing Cataract

In some embodiments, the invention provides a method of treating or preventing cataract, the method comprising administering to an individual in need thereof an effective amount of a composition comprising a compound of any one of structural formulae I, IA, IB, or II, or e.g., a compound in Table 1. In some embodiments, the cataract is an age-related cataract, a diabetic cataract, a cataract associated with surgery, a cataract resulting from exposure to radiation, a cataract resulting from a genetic illness, a cataract resulting from an infection, or a cataract resulting from medication. In some embodiments, the individual has a hereditary form of cataract with early onset. For example, hereditary forms of cataract include individuals with a R120G mutation and/or a D109H mutation in cryAB.

An individual "in need of" treatment according to the invention is an individual that is suffering from a cataract. For example, the individual may have an age-related cataract or a cataract resulting from having diabetes. Similarly, an individual "in need of" treatment according to the invention is an individual that is at risk for developing a cataract. Individuals at risk of developing a cataract include, but are not limited to, individuals with a family history of developing cataracts, individuals with a mutation linked to a cataract with early onset, such as individuals with a R120G mutation and/or a D109H mutation in cryAB, individuals exposed to radiation, diabetics, and the like. For example, in one aspect, the individual has been diagnosed with cataract in one eye, and the compound is administered to prevent or slow cataract formation in the contralateral eye.

"Treating" cataract does not require a 100% abolition of a cataract. Similarly, "prevention" does not require 100% inhibition of cataract formation. Any decrease in cloudiness or deceleration of cataract progression constitutes a beneficial biological effect in a subject. In this regard, the invention reduces the cataract, e.g., at least about 5%, at least about 10% or at least about 20% compared to levels observed in the absence of the inventive method (e.g., in a biologically-matched control subject or specimen that is not exposed to the compound of the inventive method). In some embodiments, the cataract is reduced by at least about 30%, at least about 40%, at least about 50%, or at least about 60%, at least about 70%, at least about 80%, at least about 90%, or more (about 100%).

In some embodiments, the "treating" cataracts according to inventive method inhibits cataract formation by, e.g., at least about 5%, at least about 10% or at least about 20% compared to levels observed in the absence of the inventive method (e.g., in a biologically-matched control subject or specimen that is not exposed to the compound of the inventive method). In some embodiments, cataract formation is inhibited by at least about 30%, at least about 40%, at least about 50%, or at least about 60%, at least about 70%, at least about 80%, at least about 90%, or more (about 100%) compared to cataract formation in the absence of the compound of the inventive method. Cataracts generally are detected using any of a number of optic tests including, but not limited to, visual acuity testing, ophthalmoscopy, slit-lamp examination, keratometry, tonometry, contrast testing, glare sensitivity, wavefront mapping.

An "effective amount" of a composition comprising a compound of any one of structural formulae I, IA, IB, or II, or a compound in Table 1 is an amount that inhibits or reduces aggregation of an amyloid-forming protein such as cryAB in an individual. Inhibiting aggregation does not require a 100% inhibition of aggregation. Any inhibition of aggregation constitutes a beneficial biological effect in a subject. In this regard, the invention inhibits the aggregation of an amyloid-forming protein, e.g., at least about 5%, at least about 10% or at least about 20% compared to levels observed in the absence of the inventive method (e.g., in a biologically-matched control subject or specimen that is not exposed to the compound of the inventive method). In some embodiments, the formation of amyloid aggregates is inhibited by at least about 30%, at least about 40%, at least about 50%, or at least about 60%. In some embodiments, the inventive method inhibits amyloid formation by at least about 70%, at least about 80%, at least about 90%, or more (about 100%) compared to amyloid formation in the absence of the compound of the inventive method.

Similarly, an "effective amount" for reducing aggregation does not require a 100% abolition of aggregation. Any reduction of aggregation constitutes a beneficial biological effect in a subject. In this regard, the invention reduces the aggregation of an amyloid-forming protein, e.g., at least about 5%, at least about 10% or at least about 20% compared to levels observed in the absence of the inventive method (e.g., in a biologically-matched control subject or specimen that is not exposed to the compound of the inventive method). In some embodiments, amyloid aggregates are reduced by at least about 30%, at least about 40%, at least about 50%, or at least about 60%. In some embodiments, the inventive method reduces amyloid aggregates by at least about 70%, at least about 80%, at least about 90%, or more (about 100%) compared to amyloid aggregates in the absence of the compound of the inventive method.

Route of Administration

As will be understood by those skilled in the art, the most appropriate method of administering a compound to a subject is dependent on a number of factors. In various embodiments, the compound according to the invention is administered locally to the eye, e.g., topically, subconjunctivally, retrobulbarly, periocularly, subretinally, suprachoroidally, or intraocularly. For example, in various embodiments, the composition is delivered locally to the eye via injection. Injectable solutions can be directly injected into the cornea, crystalline lens and vitreous or their adjacent tissues using a fine needle. The composition also can be administered as an intraocular perfusate.

Additional contemplated routes of administration include, but are not limited to, one or more of: oral (e.g., as a tablet, capsule, or as an ingestible solution), mucosal (e.g., as a nasal spray or aerosol for inhalation), nasal, parenteral (e.g., by an injectable form), gastrointestinal, intraspinal, intraperitoneal, intramuscular, intravenous, intrauterine, intradermal, intracranial, intratracheal, intravaginal, intracerebroventricular, intracerebral, subcutaneous, transdermal, rectal, buccal, epidural and sublingual.

In some embodiments, the mode for delivery of a composition of the invention to the eye is via a contact lens. The lens may be provided pre-treated with the desired compound. Alternatively, the lens is provided in a kit with components for preparing a coated lens, which are provided as lyophilized powders for reconstitution or as concentrated or ready-to-use solutions. The compositions can be provided as kits for single or multi-use.

In some embodiments, the mode for delivery of a composition of the invention to the eye is via an ophthalmic rod (Gwon et al., *Ophthalmology*. 1986 September; 93(9 Suppl): 82-5). In some embodiments, the mode for delivery of a composition of the invention to the eye is via an intraocular lens-hydrogel assembly (Garty et al., *Invest Ophthalmol Vis Sci,* 2011 Aug. 3; 52(9):6109-16).

Dose

The composition comprising the compound is provided in a therapeutically effective amount that achieves a desired biological effect at a medically-acceptable level of toxicity. The dosage of the compositions may vary depending on the route of administration and the severity of the disease. The dosage may also be adjusted depending on the body weight, age, sex, and/or degree of symptoms of each patient to be treated. The precise dose and route of administration will ultimately be at the discretion of the attendant physician or veterinarian. It will be appreciated that it may be necessary to make routine variations to the dosage depending on the age and weight of the patient as well as the severity of the condition to be treated. The frequency of administration depends on the formulation and the aforementioned parameters. For example, it may be desirable to apply eye drops at least once per day, including 2, 3, 4, or 5 times per day.

Exemplary doses of the compounds for administration to a human (of approximately 70 kg body weight) via an ocular route are 0.1 mg to 1 g, e.g., 1 mg to 500 mg of the compound per unit dose. In various embodiments, the dose is about 1 µg/kg body weight to 15 mg/kg body weight. For example, the dose can be 1 µg/kg, 5 µg/kg, 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 120 µg/kg, 140 µg/kg, 160 µg/kg, 180 µg/kg, 200 µg/kg, 300 µg/kg, 400 µg/kg, 500 µg/kg, 600 µg/kg, 700 µg/kg, 800 µg/kg, 900 µg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg. Exemplary doses of the compounds for administration to a human (of approximately 70 kg body weight) via systemic route are 0.1 mg to 5 g, e.g., 1 mg to 2.5 g of the compound per unit dose.

Preferred concentrations of the compound of formula I, IA, IB, or II, or a compound listed in Table 1, range from about 1 µg/ml to 500 µg/ml, for example, about 1 µg/ml, about 2 µg/ml, about 3 µg/ml, about 4 µg/ml, about 5 µg/ml, about 10 µg/ml, about 20 µg/ml, about 30 µg/ml, about 40 µg/ml, about 50 µg/ml, about 60 µg/ml, about 70 µg/ml, about 80 µg/ml, about 90 µg/ml, about 100 µg/ml, about 120 µg/ml, about 140 µg/ml, about 160 µg/ml, about 180 µg/ml, about 200 µg/ml, about 250 µg/ml, about 300 µg/ml, about 350 µg/ml, about 400 µg/ml, about 450 µg/ml, or about 500 µg/ml. The inhibitor may be provided in combination with other pharmaceutically active agents.

The composition according to the invention is provided in a container, either as a concentrate that is diluted prior to use in an appropriate diluent or at the ready-to-use concentration. Preferably, single dosages are provided in sterile vials.

Compounds Effective in Treating or Preventing Cataract

In various embodiments, the compound of the inventive method or composition is a compound of formula I:

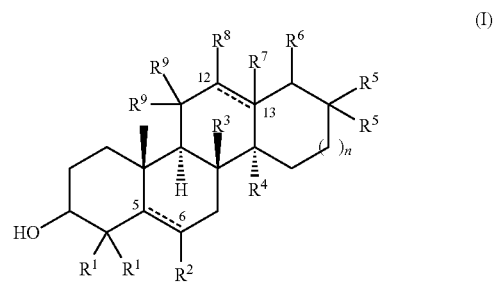

(I)

wherein:

both $R^1$ are H or both $R^1$ are Me;

$R^2$ is H or OH;

dashed line between carbons 5 and 6 indicates an optional double bond;

$R^3$ is H or Me;

$R^4$ is H or Me;

n is 0 or 1;

(a) $R^6$ is

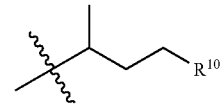

and each $R^5$ is independently H or Me or (b) $R^6$ and one $R^5$ taken together form an optionally substituted 6-membered ring and the other $R^5$ is Me;

the dashed line between carbons 12 and 13 is an optional double bond, with the proviso that $R^7$ is not present when the double bond between carbons 12 and 13 is present, and $R^7$ is H or Me when the double bond between carbons 12 and 13 is not present;

$R^8$ is H or OH;

both $R^9$ together form an oxo (=O) or both $R^9$ are hydrogen; and $R^{10}$ is $CO_2H$ or linear or branched $C_1$-$C_6$ alkyl.

For example, the compound of the inventive method or composition is a compound of formula IA or formula IB:

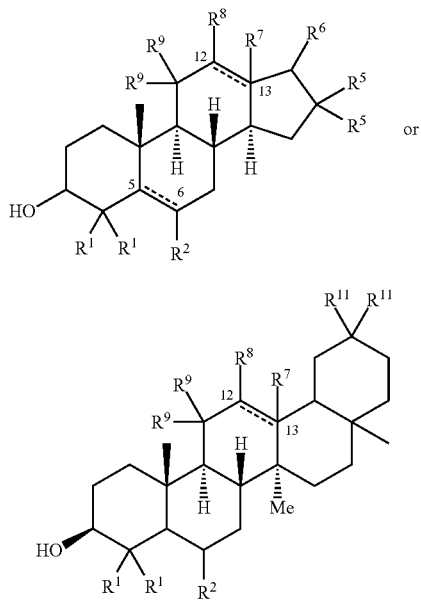

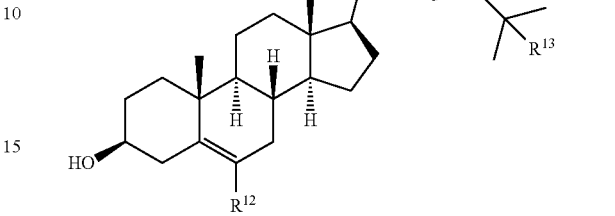

wherein each $R^{11}$ is independently alkyl, $CO_2H$, or $CO_2$alkyl.

In various embodiments, the compound has a structure of formula II:

wherein $R^{12}$ is H or OH and $R^{13}$ is H or OH. In some embodiments, the compound is 5-cholestin-3b,25-diol.

Alternatively, the compound is a compound listed in Table 1.

Any prodrug or pharmaceutically acceptable salt of the above compounds are contemplated to be within the scope of the invention.

TABLE 1

| STRUCTURE | CCG ID | NAME | IUPAC |
|---|---|---|---|
| 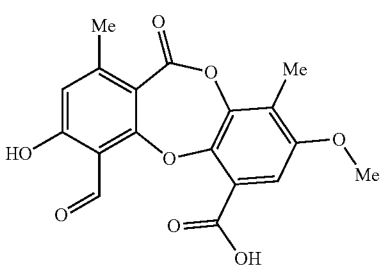 [SMILES: COc1cc(C(=O)O)c2c(c1C)OC(=O)c1c(C)cc(O)c(C=O)c1O2] | 38361 | PSOROMIC ACID | 15-formyl-14-hydroxy-6-methoxy-7,12-dimethyl-10-oxo-2,9-dioxatricyclo[9.4.0.0^{3,8}]pentadeca-1(11),3(8),4,6,12,14-hexaene-4-carboxylic acid |
| 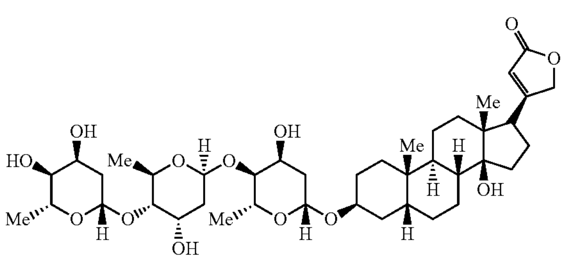 | 38362 | DIGITOXIN | 4-[(2S,5S,7R,11S,14R,15R)-5-{[(2R,4S,5S,6R)-5-{[(2S,4S,5S,6R)-5-{[(2S,4S,5S,6R)-4,5-dihydroxy-6-methyloxan-2-yl]oxy}-4-hydroxy-6-methyloxan-2-yl]oxy}-4-hydroxy-6-methyloxan-2-yl]oxy}-11-hydroxy-2,15-dimethyltetracyclo[8.7.0.0^{2,7}.0^{11,15}]heptadecan-14-yl]-2,5-dihydrofuran-2-one |
| 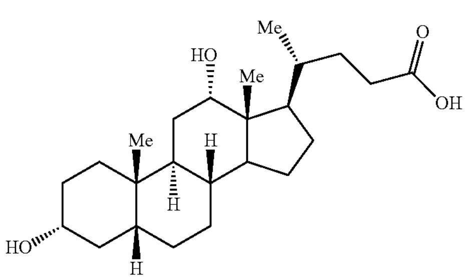 | 38631 | DEOXY-CHOLIC ACID | (4R)-4-[(2S,5R,7R,14R,15R,16S)-5,16-dihydroxy-2,15-dimethyltetracyclo[8.7.0.0^{2,7}.0^{11,15}]heptadecan-14-yl]pentanoic acid |

TABLE 1-continued

| STRUCTURE | CCG ID | NAME | IUPAC |
|---|---|---|---|
| 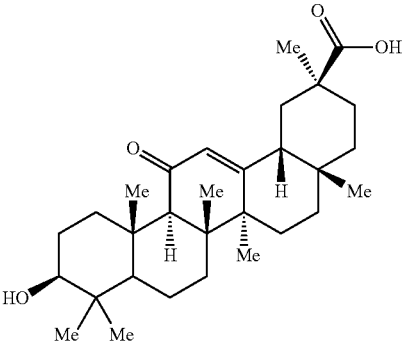 | 38703 | ENOXOLONE | (2S,4aS,6aS,6bR,10S,12aS,14bR)-10-hydroxy-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid |
| 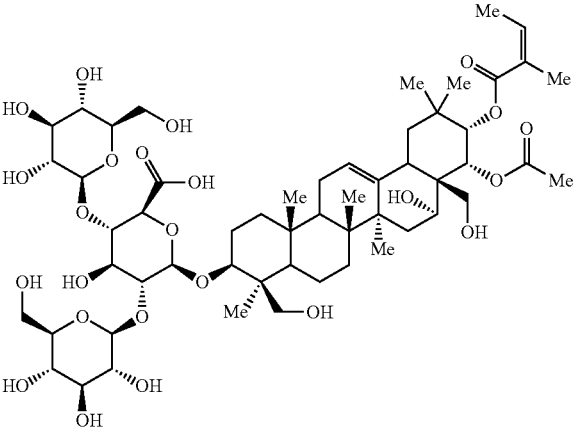 | 38719 | beta-ESCIN | (2S,3S,4S,5R,6R)-6-{[(3S,4S,6aR,6bS,8R,8aR,9R,10S,14bR)-9-(acetyloxy)-8-hydroxy-4,8a-bis(hydroxymethyl)-4,6a,6b,11,11,14b-hexamethyl-10-{[(2Z)-2-methylbut-2-enoyl]oxy}-1,2,3,4,4a,5,6,6a,6b,7,8,8a,9,10,11,12,12a,14,14a,14b-icosahydropicen-3-yl]oxy}-4-hydroxy-3,5-bis({[(2S,3R,4S,5S,6R)-3,4,5-trihydroxy-6-(hydroxymethyl)oxan-2-yl]oxy})oxane-2-carboxylic acid |
| 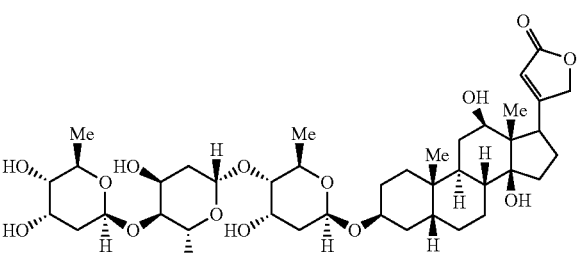 | 38826 | DIGOXIN | 4-[(2S,5S,7R,11S,14R,15S,16R)-5-{[(2R,4S,5S,6R)-5-{[(2S,4S,5S,6R)-5-{[(2S,4S,5S,6R)-4,5-dihydroxy-6-methyloxan-2-yl]oxy}-4-hydroxy-6-methyloxan-2-yl]oxy}-4-hydroxy-6-methyloxan-2-yl]oxy}-11,16-dihydroxy-2,15-dimethyltetracyclo[8.7.0.0^{2,7}.0^{11,15}]heptadecan-14-yl]-2,5-dihydrofuran-2-one |
| 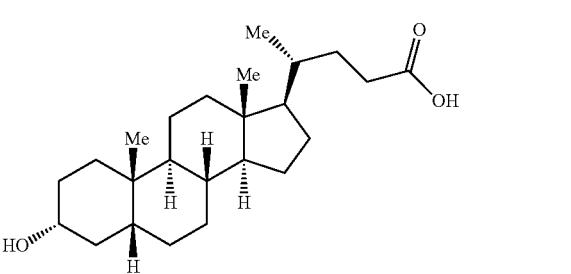 | 38850 | LITHO-CHOLIC ACID | (4R)-4-[(2S,5R,7R,14R,15R)-5-hydroxy-2,15-dimethyl-tetracyclo[8.7.0.0^{2,7}.0^{11,15}]heptadecan-14-yl]pentanoic acid |
| 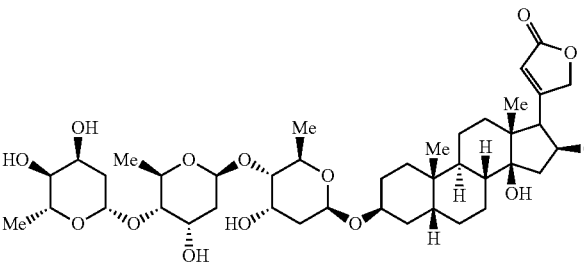 | 38852 | GOTOXIN | 4-[(2S,5S,7R,10R,11S,13S,14R,15R)-5-{[(2R,4S,5S,6R)-5-{[(4S,5S,6R)-5-{[(4S,6R)-4,5-dihydroxy-6-methyloxan-2-yl]oxy}-4-hydroxy-6-methyloxan-2-yl]oxy}-4-hydroxy-6-methyloxan-2-yl]oxy}-11,13-dihydroxy-2,15-dimethyltetracyclo[8.7.0.0^{2,7}.0^{11,15}]heptadecan-14-yl]-2,5-dihydrofuran-2-one |

TABLE 1-continued

| STRUCTURE | CCG ID | NAME | IUPAC |
|---|---|---|---|
| 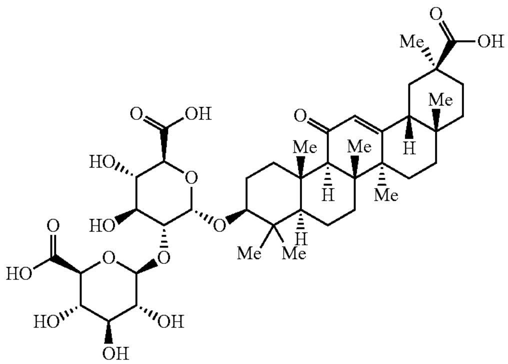 | 38857 | GLYCYR-RHIZIC ACID | (2S,3S,4S,5R,6R)-6-(((2S,3R,4S,5S,6S)-6-carboxy-2-(((3S,4aR,6aR,6bS,8aS,11S,12aR,14aR,14bS)-11-carboxy-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)oxy)-4,5-dihydroxytetrahydro-2H-pyran-3-yl)oxy)-3,4,5-trihydroxytetrahydro-2H-pyran-2-carboxylic acid |
| 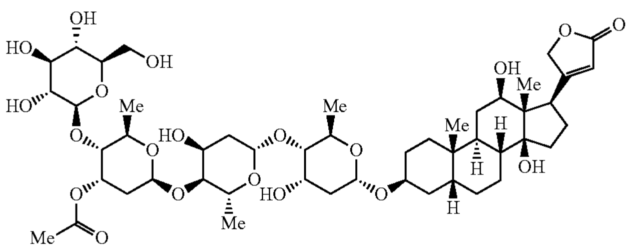 | 38866 | LANATO-SIDE C | (2R,3R,4S,6S)-6-{[(2R,3S,4S,6S)-6-{[(2R,3S,4S,6R)-6-{[(2S,5S,11S,14R,15S,16R)-11,16-dihydroxy-2,15-dimethyl-14-(5-oxo-2,5-dihydrofuran-3-yl)tetracyclo[8.7.0.0^{2,7}.0^{11,15}]heptadecan-5-yl]oxy}-4-hydroxy-2-methyloxan-3-yl]oxy}-4-hydroxy-2-methyloxan-3-yl]oxy}-2-methyl-3-{[(2S,3R,4S,5S,6R)-3,4,5-trihydroxy-6-(hydroxymethyl)oxan-2-yl]oxy}oxan-4-yl acetate |
| 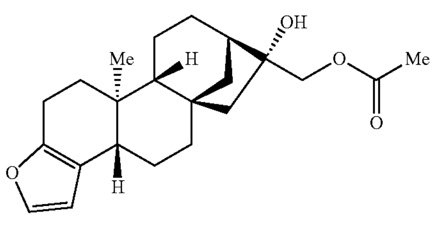 [SMILES: CC(=O)OC[C@@]1(O)C[C@]23CC[C@@H]4c5ccoc5CC[C@@]4(C)[C@@H]2CC[C@H]1C3] | 38894 | CAFESTOL ACETATE | [(1S,12R,16R,17R)-17-hydroxy-12-methyl-8-oxapentacyclo[14.2.1.0^{1,13}.0^{4,12}.0^{5,9}]nonadeca-5(9),6-dien-17-yl]methyl acetate |
| 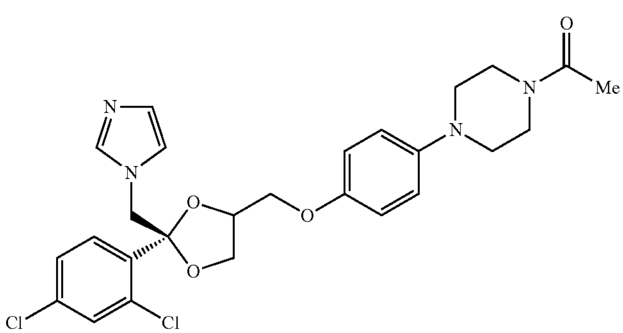 [SMILES: CC(=O)N1CCN(c2ccc(OCC3CO[C@](Cn4ccnc4)(c4ccc(Cl)cc4Cl)O3)cc2)CC1] | 38938 | KETOCONA-ZOLE | 1-[4-(4-{[(2R)-2-(2,4-dichlorophenyl)-2-(1H-imidazol-1-ylmethyl)-1,3-dioxolan-4-yl]methoxy}phenyl)piperazin-1-yl]ethan-1-one |
| 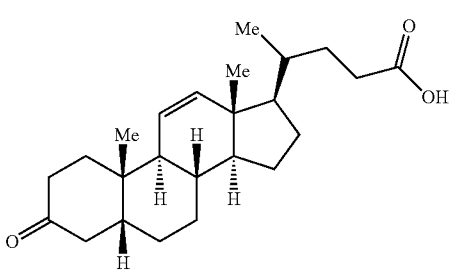 | 39166 | CHOL-11-ENIC ACID | (4R)-4-[(2S,7R,14R,15R)-2,15-dimethyl-5-oxotetracyclo[8.7.0.0^{2,7}.0^{11,15}]heptadec-16-en-14-yl]pentanoic acid |

TABLE 1-continued

| STRUCTURE | CCG ID | NAME | IUPAC |
|---|---|---|---|
| 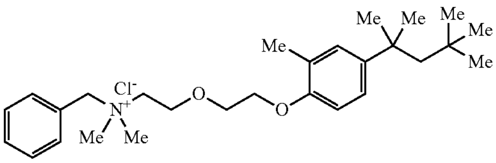 [SMILES: Cc1cc(C(C)(C)CC(C)(C)C)ccc1OCCOCC[N+](C)(C)Cc1ccccc1 ; [Cl-]] | 39322 | METHYL-BENZE-THONIUM CHLORIDE | benzyldimethyl(2-{2-[2-methyl-4-(2,4,4-trimethylpentan-2-yl)phenoxy]ethoxy}ethyl)azanium chloride |
| 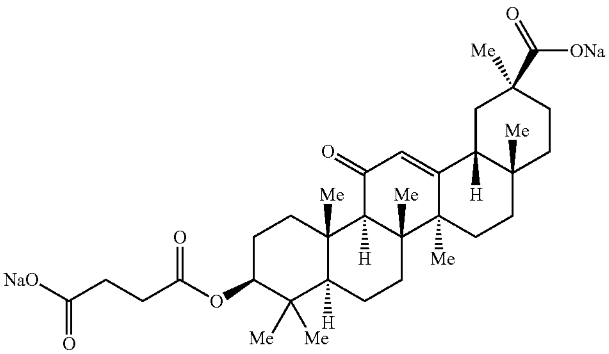 | 39682 | CARBEN-OXOLONE SODIUM | disodium(2S,4aS,6aS,6bR,10S,12aS,14bR)-10-[(3-carboxylatopropanoyl)oxy]-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate |
| 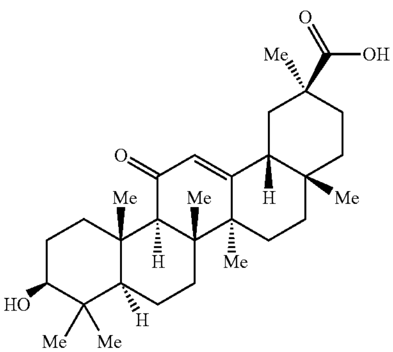 | 39958 | 18alpha-GLYCYR-RHETINIC ACID | (2S,4aS,6aS,6bR,10S,12aS,14bS)-10-hydroxy-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid |
| 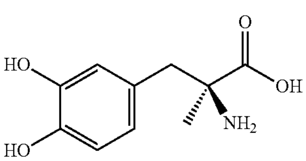 | 40120 | METHYL-DOPA | 2-amino-3-(3,4-dihydroxyphenyl)-2-methylpropanoic acid |
| 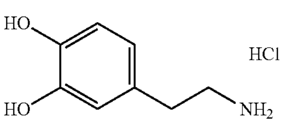 | 40211 | DOPAMINE HYDRO-CHLORIDE | 4-(2-aminoethyl)benzene-1,2-diol hydrochloride |
| 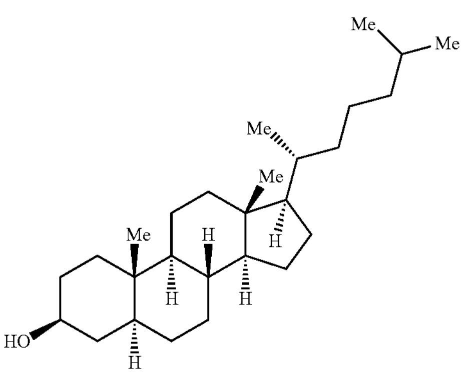 | 40270 | 5alpha-CHOLESTAN-3beta-OL-6-ONE | (2R,5S,7S,15R)-5-hydroxy-2,15-dimethyl-14-(6-methylheptan-2-yl)tetracyclo[8.7.0.0^{2,7}.0^{11,15}]heptadecan-8-one |

TABLE 1-continued

| STRUCTURE | CCG ID | NAME | IUPAC |
|---|---|---|---|
| 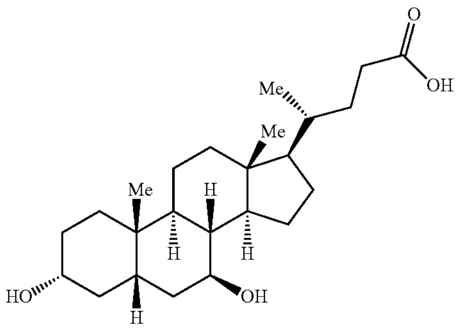 | 40274 | URSODIOL | (4R)-4-[(2S,5R,7S,9S,14R,15R)-5,9-dihydroxy-2,15-dimethyltetracyclo[8.7.0.0^{2,7}.0^{11,15}]heptadecan-14-yl]pentanoic acid |
| 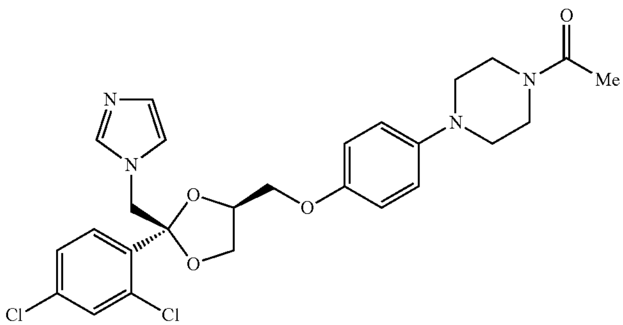 [SMILES: CC(=O)N1CCN(c2ccc(OC[C@H]3CO[C@](Cn4ccnc4)(c4ccc(Cl)cc4Cl)O3)cc2)CC1] | 100815 | CPD000058460_KETOCONAZOLE | 1-[4-(4-{[(2R,4S)-2-(2,4-dichlorophenyl)-2-(1H-imidazol-1-ylmethyl)-1,3-dioxolan-4-yl]methoxy}phenyl)piperazin-1-yl]ethan-1-one |
| 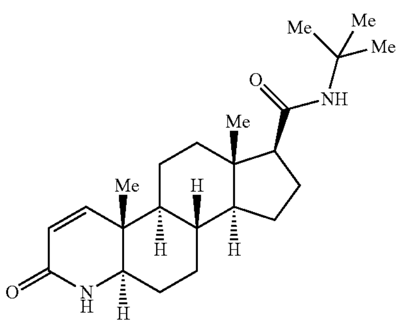 | 100937 | CPD000466304_FINASTERIDE | (1S,2R,7R,10S,11S,14S,15S)-N-tert-butyl-2,15-dimethyl-5-oxo-6-azatetracyclo[8.7.0.0^{2,7}.0^{11,15}]heptadec-3-ene-14-carboxamide |
| 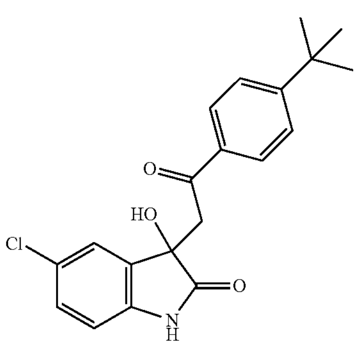 [SMILES: CC(C)(C)c1ccc(C(=O)CC2(O)C(=O)Nc3ccc(Cl)cc32)cc1] | 22428 | | 3-[2-(4-tert-butylphenyl)-2-oxoethyl]-5-chloro-3-hydroxy-2,3-dihydro-1H-indol-2-one |
| 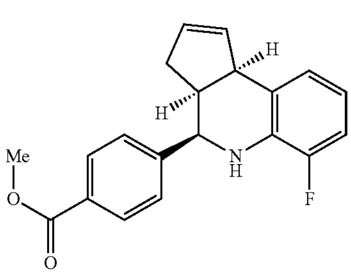 [SMILES: COC(=O)c1ccc([C@@H]2Nc3c(F)cccc3[C@@H]3C=CC[C@@H]32)cc1] | 22775 | | methyl 4-[(2R,6S,7R)-10-fluoro-8-azatricyclo[7.4.0.0^{2,6}]trideca-1(13),3,9,11-tetraen-7-yl]benzoate |

TABLE 1-continued

| STRUCTURE | CCG ID | NAME | IUPAC |
|---|---|---|---|
| 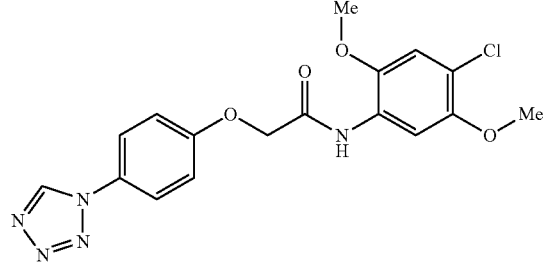 [SMILES: COc1cc(NC(=O)COc2ccc(-n3cnnn3)cc2)c(OC)cc1Cl] | 108668 | | N-(4-chloro-2,5-dimethoxyphenyl)-2-[4-(1H-1,2,3,4-tetrazol-1-yl)phenoxy]acetamide |
| 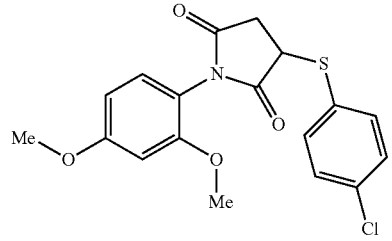 [SMILES: COc1ccc(N2C(=O)CC(Sc3ccc(Cl)cc3)C2=O)c(OC)c1] | 109888 | | 3-[(4-chlorophenyl)sulfanyl]-1-(2,4-dimethoxyphenyl)pyrrolidine-2,5-dione |
| 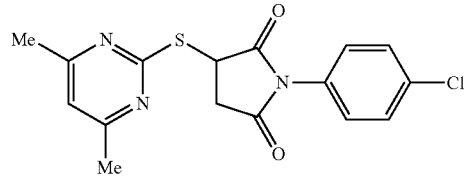 [SMILES: Cc1cc(C)nc(SC2CC(=O)N(c3ccc(Cl)cc3)C2=O)n1] | 112216 | | 1-(4-chlorophenyl)-3-[(4,6-dimethylpyrimidin-2-yl)sulfanyl]pyrrolidine-2,5-dione |
| 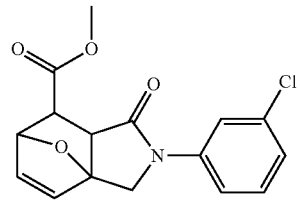 [SMILES: COC(=O)C1C2C=CC3(CN(c4cccc(Cl)c4)C(=O)C13)O2] | 116781 | | methyl 3-(3-chlorophenyl)-4-oxo-10-oxa-3-azatricyclo[5.2.1.0^{1,5}]dec-8-ene-6-carboxylate. |

Pharmaceutical Compositions

The invention further comprises a composition comprising the compound of any one of structural formulae I, IA, IB, or II, or a compound listed in Table 1, and a pharmaceutically acceptable ophthalmic carrier, e.g., a pharmaceutically acceptable excipient, carrier, binder, and/or diluent. Optionally, the composition includes a free acid, free base, salt (e.g., an acid or base addition salt), hydrate or prodrug of the compound of any one of structural formula I, IA, IB, or II, or a compound listed in Table 1. The prodrug is a material that includes the compound in any one of structural formulae I, IA, IB, or II, or a compound listed in Table 1, covalently bound to a carrier moiety. The carrier moiety can be released from the compound in any one of structural formulae I, IA, IB, or II, or a compound listed in Table 1, in vitro or in vivo to yield compound in any one of structural formula I, IA, IB, or II, or a compound listed in Table 1. Prodrug forms are well known in the art as exemplified in Sloan, K. B., *Prodrugs*, M. Dekker, New York, 1992; and Testa, B. and Mayer, J. M., *Hydrolysis in drug and prodrug metabolism: chemistry, biochemistry, and enzymology*, Wiley-VCH, Zurich, 2003.

In various embodiments, the composition comprises the compound of any one of structural formulae I, IA, IB, or II, or a compound listed in Table 1, formulated as eye drops, injectable solutions or eye ointments. These pharmaceutical compositions can be formulated by admixing, diluting or dissolving the compound, optionally, with appropriate pharmaceutical additives such as excipients, disintegrators, binders, lubricants, diluents, buffers, antiseptics, moistening agents, emulsifiers, dispersing agents, stabilizing agents and dissolving aids in accordance with conventional methods and formulating in a conventional manner depending upon the dosage form. For example, eye drops can be formulated by dissolving the compound in sterilized water in which a surface active agent is dissolved and optionally adding appropriate pharmaceutical additives such as a preservative, a stabilizing agent, a buffer, an antioxidant and a viscosity improver. In some embodiments, the composition includes a cyclodextrin. In a specific embodiment, the cyclodextrin is (2-hydroxypropyl)-β-cyclodextrin.

Physiologically acceptable buffers include, but are not limited to, a phosphate buffer or a Tris-HCl buffer (comprising tris(hydroxymethyl)aminomethane and HCl). For example, a Tris-HCl buffer having pH of 7.4 comprises 3 g/l of tris(hydroxymethyl)aminomethane and 0.76 g/l of HCl. In yet another aspect, the buffer is 10× phosphate buffer saline ("PBS") or 5×PBS solution.

Other buffers include, but are not limited to, buffers based on HEPES (N-{2-hydroxyethyl}peperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid) having $pK_a$ of 7.2 at 25° C. and pH in the range of about 6.5-7.9; TES (N-tris{hydroxymethyl}-methyl-2-aminoethanesulfonic acid) having $pK_a$ of 7.4 at 25° C. and pH in the range of about 6.8-8.2; MOBS (4-{N-morpholino}butanesulfonic acid) having $pK_a$ of 7.6 at 25° C. and pH in the range of about 6.9-8.3; DIPSO (3-(N,N-bis{2-hydroxyethyl}amino)-2-hydroxypropane)) having $pK_a$ of 7.52 at 25° C. and pH in the range of about 7-8.2; TAPS (((2-hydroxy-3{tris(hydroxymethyl)methylamino}-1-propanesulfonic acid)) having $pK_a$ of 7.61 at 25° C. and pH in the range of about 7-8.2; TAPS ({(2-hydroxy-1,1-bis(hydroxymethyl)ethyl)amino}-1-propanesulfonic acid)) having $pK_a$ of 8.4 at 25° C. and pH in the range of about 7.7-9.1; TABS (N-tris(hydroxymethyl) methyl-4-aminobutanesulfonic acid) having $pK_a$ of 8.9 at 25° C. and pH in the range of about 8.2-9.6; AMPSO (N-(1,1-dimethyl-2-hydroxyethyl)-3-amino-2-hydroxypropanesulfonic acid)) having $pK_a$ of 9.0 at 25° C. and pH in the range of about 8.3-9.7; CHES (2-cyclohexylamino)ethanesulfonic acid) having $pK_a$ of 9.5 at 25° C. and pH in the range of about 8.6-10.0; CAPSO (3-(cyclohexylamino)-2-hydroxy-1-propanesulfonic acid) having $pK_a$ of 9.6 at 25° C. and pH in the range of about 8.9-10.3; and CAPS (3-(cyclohexylamino)-1-propane sulfonic acid) having $pK_a$ of 10.4 at 25° C. and pH in the range of about 9.7-11.1.

A number of effective methods for controlled release of an active agent are available. See, for example, Wagh V. D., Inamdar B., Samanta M. K., Polymers used in ocular dosage form and drug delivery systems. *Asian J Pharm* 2, 2008, 12-17 and the literature references cited therein, the contents of which are incorporated herein by reference. The use of polymers (e.g., cellulose derivatives such as hydroxypropylmethylcellulose (HPMC) and hydroxypropylcellulose (HPC), poly(acrylic acid) (PAA), polyacrylates, cyclodextrins and natural gums, polyorthoesters (POEs) and mucoadhesive polymers); semisolids such as gels, films and other inserts; resins such as ion exchange resins; iontophoretic delivery; and colloidal particles such as microspheres and nanoparticles, are specifically contemplated.

The compounds of the invention may also be provided in combination with other therapeutic agents. In some embodiments, the compounds of the invention may be co-formulated with a pain reliever, an anesthetic, artificial tears, an enzyme inhibitor, a cytokine inhibitor, an anti-inflammatory, or an antibiotic In some embodiments, the antibiotic is an antibacterial, antiviral, antifungal, antiprotozoal agent, or a combination thereof.

In various embodiments, the compounds of the invention may also be provided in combination with an ocular therapeutic selected from the group consisting of Acular (ketorolac tromethamine ophthalmic solution) 0.5%, Acuvail (ketorolac tromethamine), AK-Con-A (naphazoline ophthalmic), Akten (lidocaine hydrochloride), Alamast, Alphagan (brimonidine), Alrex, Astepro (azelastine hydrochloride nasal spray), AzaSite (azithromycin), Bepreve (bepotastine besilate ophthalmic solution), Besivance (besifloxacin ophthalmic suspension), Betaxon, BSS Sterile Irrigating Solution, Cosopt, Durezol (difluprednate), Eylea (aflibercept), Lotemax, Lucentis (ranibizumab), Lumigan (bimatoprost ophthalmic solution), Macugen (pegaptanib), Ocuflox (ofloxacin opthalmic solution) 0.3%, OcuHist, Ozurdex (dexamethasone), Quixin (levofloxacin), Rescula (unoprostone isopropyl ophthalmic solution) 0.15%, Restasis (cyclosporine ophthalmic emulsion), Salagen Tablets, Travatan (travoprost ophthalmic solution), Valcyte (valganciclovir HCl), Viroptic, Vistide (cidofovir), Visudyne (verteporfin for injection), Vitrasert Implant, Vitravene Injection, ZADITOR, Zioptan (tafluprost ophthalmic solution), Zirgan (ganciclovir ophthalmic gel), Zymaxid (gatifloxacin ophthalmic solution), Atropine, Flurbiprofen, Physostimine, Azopt, Gentamicin, Pilocarpine, Bacitracin, Goniosol, Polymyxin B, Betadine, Gramicidin, Prednisolone, Betaxolol, Humorsol, Proparacaine, Betoptic, Hylartin, Propine, Brinzolamide, Hypertonic NaCl, Puralube, BSS, Indocycanine Green, Rose Bengal, Carbachol, Itraconazole, Sodium Hyaluronate, Cefazolin, Latanoprost, Suprofen, Celluvisc, Mannitol, Terramycin, Chloramphenicol, Methazolamide, Timolol, Ciloxan, Miconazole, Tobramycin, Ciprofloxacin, Miostat, Triamcinolone, Cosopt, Muro 128, Trifluridine, Demecarium, Neomycin, Tropicamide, Dexamethasone, Neptazane, Trusopt, Dipivefrin, Ocuflox, Vidarabine, Dorzolamide, Ofloxacin, Vira-A, Epinephrine, Oxytetracycline, Viroptic, Fluorescein, Phenylephrine, and Xalatan.

Screening Methods and Systems

In various embodiments, the invention includes a high-throughput method of screening compounds for modulation of protein thermal stability. The method comprises (a) contacting a protein with each of a plurality of test compounds; and (b) measuring the melting transition ($T_m$) of the protein in the presence of each of the plurality of test compounds, wherein a compound that decreases or increases the apparent $T_m$ by at least 2 standard deviations is a pharmacological protein chaperone. In various embodiments, a compound that decreases or increases the apparent $T_m$ by at least 3 standard deviations is a pharmacological protein chaperone.

An agent that modulates protein thermal stability can be identified using differential scanning fluorimetry (DSF). In DSF, the melting transition ($T_m$) of the protein target is measured in the presence of potential ligand. DSF measures thermal unfolding of the target protein via the fluorescence of intrinsic tryptophans, or a dye, such as 1,8-anilinonaphtalenesulfonic (bis-ANS) or Sypro Orange. Binding of a ligand adds free energy to the folded state or key intermediates, which limits unfolding and shifts the apparent $T_m$. Thus, in some embodiments, the melting transition is determined using a high-throughput differential scanning fluorimetry device, such as a ThermoFluor® 384-well DSF platform, or a real-time PCT thermocycler.

In various embodiments of the screening method, the step wherein the melting transition is measured comprises the following steps: (b1) heating the protein in the presence of each of a plurality of test compounds from 50° C. to 80° C., (b2) cooling the protein to 25° C., (b3) maintaining the protein at 25° C. for 10 seconds, and (b4) measuring the fluorescence of the protein. In more specific embodiments, the method further comprises repeating steps (b1)-(b4) between 2 and 30 times, wherein each repeat of step (b1) is performed at an incrementally higher temperature. For example, during the first iteration, the protein is heated to 65° C. in the presence of a test compound and cooled to 25° C. where it is maintained for about 10 seconds before the fluorescence of the protein is measured. During the second iteration, the protein is heated to 66° C. in the presence of a test compound and cooled to 25° C. where it is maintained for about 10 seconds before the fluorescence of the protein is measured. This process is repeated (e.g., between 2 and 30 times) while increasing the peak temperature to which the protein is heated, e.g., in 1° C. increments. In some embodiments, during step (b1), the protein is equilibrated at the peak temperature between 60 and 180 seconds. In specific embodiments of the method, the equilibrating step is 130 seconds.

In various embodiments of the screening method, the step wherein the melting transition is measured comprises gradually heating the protein in the presence of each of a plurality of test compounds to 80° C. while continuously measuring the fluorescence of the protein.

In various aspects of the screening method, the protein is an amyloid-forming protein. Generally, when the protein is an amyloid-forming protein, the desired modulator decreases the melting transition of the protein. Such a modulator stabilizes the non-amyloid form of the protein. In some embodiments, the amyloid-forming protein is selected from the group consisting of Hsp27, αA-crystallin (cataract), αB-crystallin (cataract), βB2-crystallin (cataract), βB1-crystallin (cataract), γD-crystallin (cataract), Hsp22, Hsp20, tau, Alpha-synuclein (Parkinson's disease), IAPP (Diabetes mellitus type 2), beta-amyloid (Alzheimer's disease), PrP (Transmissible spongiform encephalopathy), Huntingtin (Huntington's Disease), Calcitonin (Medullary carcinoma of the thyroid), Atrial natriuretic factor (Isolated atrial amyloidosis), Apolipoprotein AI (Atherosclerosis), Serum amyloid A (Rheumatoid arthritis), Medin (Aortic medial amyloid), Prolactin (Prolactinomas), Transthyretin (Familial amyloid polyneuropathy), Lysozyme (Hereditary non-neuropathic systemic amyloidosis), Beta 2 microglobulin (Dialysis related amyloidosis), Gelsolin (Finnish amyloidosis), Keratoepithelin (Lattice corneal dystrophy), Cystatin (Cerebral amyloid angiopathy: Icelandic type), Immunoglobulin light chain AL (systemic AL amyloidosis), myocilin (glaucoma), and S-IBM (Sporadic Inclusion Body Myositis).

In some embodiments of the screening method, the protein is a protein underlying a loss-of-function disease. Generally, when the protein is a protein underlying a loss-of-function disease, the desired modulator increases the melting transition of the protein. Such a modulator stabilizes the mutant form of the protein such that it remains active (i.e., degradation of the protein is reduced). The protein underlying a loss-of-function disease can be, for example, mutant β-glucosidase, mutant glucosylceramidase (Gaucher's disease), mutant cystic fibrosis transmembrane receptor (cystic fibrosis), mutant hexosaminidase A (Tay-Sachs disease), mutant hexosaminidase B (Sandhoff disease), mutant β-galactosidase (Morquio syndrome), and mutant alpha-glucosidase (i.e., Pompe disease).

In some embodiments, the invention includes a high-throughput screening system, comprising: (a) an amyloid-forming protein; (b) a device capable of measuring the melting transition ($T_m$) of the amyloid-forming protein; and (c) a plurality of test compounds. The device capable of measuring the $T_m$ of the amyloid-forming protein can be any device known in the art. As noted above, in some embodiments, the device is a differential scanning fluorimetry device, such as a ThermoFluor® 384-well DSF platform. In various aspects of the screening system, the protein is selected from the group consisting of Hsp27, αA-crystallin, αB-crystallin, βB2-crystallin, βB1-crystallin, γD-crystallin, Hsp22, Hsp20, tau, Alpha-synuclein, IAPP, beta-amyloid, PrP, Huntingtin, Calcitonin, Atrial natriuretic factor, Apolipoprotein AI, Serum amyloid A, Medin, Prolactin, Transthyretin, Lysozyme, Beta 2 microglobulin, Gelsolin, Keratoepithelin, Cystatin, Immunoglobulin light chain AL, and S-IBM.

EXAMPLES

The following are non-limiting examples of various aspects of the methods described herein. The examples are given solely for the purpose of illustration and are not to be construed as limiting the disclosure, as many variations thereof are possible.

Example 1

This Example describes a high-throughput method of screening for compounds that stabilize an exemplary aggregation-prone protein, Hsp27.

Differential scanning fluorimetry (DSF) was utilized to identify compounds that stabilize cryAB. In DSF experiments, the melting transition ($T_m$) of the protein target is measured in the presence of potential ligands (Cummings et al., *J Biomol Screen* 11, 854 (2006). DSF measures thermal unfolding of the target protein via the fluorescence of intrinsic tryptophans, or (more commonly) a dye, such as 1,8-anilinonapthalenesulfonic (bis-ANS) or Sypro Orange. Binding of a ligand adds free energy to the folded state or key intermediates, which limits unfolding and shifts the apparent $T_m$. These values are used to calculate the unfolding transition. When compounds bind to the target prior to heating, they stabilize against unfolding, shifting the ΔTm. For the case of cryAB and the cryAB R120G mutant, compounds that reduced the apparent $T_m$ were sought, because amyloids typically have a higher apparent stability in this platform. For example, the $T_m$ of wild type cryAB was 64.1±0.5° C., whereas the more amyloid-prone R120G cryAB mutant had an apparent $T_m$ of 68.3±0.2° C. (3). This difference correlated with the increased amyloid propensity of R120G. Thus, it was reasoned that the screening "hits" which reduce apparent $T_m$ might suppress aggregation.

Using a miniaturized 384-well DSF platform (ThermoFluor®), 2,446 compounds were screened for the ability to block aggregation of an sHSP. As a model, human Hsp27 was used for the HTS because it readily forms amyloids and it retains the highly conserved crystallin domain found in all sHSPs. Hsp27 was soluble at room temperature, but it thermally unfolded and rapidly formed stable amyloids upon heating.

The screen was performed in 7 μL volume, with 10 μM Hsp27 in 50 mM NaPO4, pH 7.4, 700 mM NaCl, 50 mM LiCl, and 100 μM bis-ANS in Abgene black 384-well PCR plates. Reactions were covered with silicon oil to limit evaporation. Control tests suggested that the assay tolerated up to 4% DMSO but 1% was used as a final concentration. The plates were measured in up/down mode, which was empirically determined to give better signal-to-noise than the continuous ramp mode. Plates were heated from 65° C. to 80° C. in 1° C. increments, equilibrated for 130 seconds at each high temperature, cooled to 25° C., and held for 10 seconds at 25° C. prior to imaging with a single 10 second exposure for each temperature reading. Plate uniformity tests measured the $T_m$ of Hsp27 at 72.3±0.16° C. The Z factor was calculated to vary between ~0.59 and 0.71 and the CVs were 8%. Most of the variability appeared to arise from some "edge effects"

For each well, a series of fluorescence vs. temperature points were obtained, plotted and fit to determine the $T_m$. An automated method was developed in MatLab that performs the individual fits and then ranks each test well on the basis of how closely the three independent fitting methods (Savitzky-Golay derivative, sigmoidal curve and parallel baseline Hill) agree.

From the primary screen, 45 compounds were identified that decreased the apparent $T_m$ by more than three standard deviations (−3SD; ~0.6° C.) and 45 compounds increased the $T_m$ by +3SD. All 90 of these compounds were explored in dose dependence experiments to confirm their activity and, from those studies, 64 had activity below 50 µM. The 45 compounds identified that decreased the apparent $T_m$ by more than three standard deviations were tested in 12-point dose dependence assays, providing 28 that both confirmed and shifted $\Delta T_m$ at concentrations less than 20 µM. Interestingly, 12 of these 28 were part of a single structural class of related sterols. This scaffold was selected for further investigation.

Taken together, these studies validate the HTS method as a robust means for identifying pharmacological chaperones for amyloid-forming proteins, such as cryAB. Indeed, the studies validate the HTS method for finding agents that modulate $T_m$ for any protein wherein increased (e.g., loss of function proteins such as the mutant form of alpha-glucosidase responsible for Pompe Disease) or decreased stability (aggregation-prone proteins such as Huntingtin) is desired.

Example 2

This Example describes structure-activity relationship (SAR) studies of a sterol scaffold identified in the primary screen of Example 1. As described further below, the SAR revealed a general chemical structure (Formula I) for compounds that reduced the $T_m$ of an amyloid-forming protein, R120G cryAB, by at least 2° C.

Thirty-two sterols with chemical structures related to 17-a-hydroxy-progesterone were collected and subjected to further testing (see Table 2). DSF experiments on this focused collection were performed using R120G cryAB and two compounds that reduced $T_m$ by at least 2° C. were identified: 5a-cholestan-3b-ol-6-one and 5-cholesten-3b,25-diol. Many of the other closely-related sterols, including cholesterol, were inactive and the resulting SAR supported a rather specific molecular interaction.

TABLE 2

| NAME | ACTIVITY (shift in thermal stability at 100 µM) |
|---|---|
| 5-cholesten-3b,25-diol | −2.0° C. |
| 5a-cholestan-3b-ol-6-one | −3.0° C. |
| 5-cholesten-3b-ol | −1.1° C. |
| etiocholan-17b-ol-3-one | +1.7° C. |
| 17-a-hydroxy-progesterone | between +1° C. and −1° C. |
| 5a-androstan-3b,17b-diol | between +1° C. and −1° C. |
| 17a-hydroxy-pregnenolone | between +1° C. and −1° C. |
| 5-a-androstan-3,17-dione | between +1° C. and −1° C. |
| epiandrosterone | between +1° C. and −1° C. |
| progesterone | between +1° C. and −1° C. |
| dehydroisoandrosterone | between +1° C. and −1° C. |
| D4-androsten-3,17-dione | between +1° C. and −1° C. |
| b-estradiol | between +1° C. and −1° C. |
| testosterone | between +1° C. and −1° C. |
| corticosterone | between +1° C. and −1° C. |
| cortisone | between +1° C. and −1° C. |
| estriol | between +1° C. and −1° C. |
| 4-cholesten-3-one | between +1° C. and −1° C. |
| cholesterol | between +1° C. and −1° C. |
| hydrocortisone | between +1° C. and −1° C. |
| estrone | between +1° C. and −1° C. |
| D5-pregnen-3b-ol-20-one | between +1° C. and −1° C. |
| testosterone acetate | between +1° C. and −1° C. |
| deoxycorticosterone | between +1° C. and −1° C. |
| androsterone | between +1° C. and −1° C. |
| corticosterone-21-acetate | between +1° C. and −1° C. |
| digitonin | between +1° C. and −1° C. |
| 5-cholesten-3b-ol-7-one | between +1° C. and −1° C. |
| ursodeoxycholic acid | between +1° C. and −1° C. |
| 6-ketocholestanol | between +1° C. and −1° C. |
| 18-a-glycyrrhetinic acid | between +1° C. and −1° C. |

TABLE 2-continued

Further dose dependence studies with 5a-cholestan-3b-ol-6-one, 5-cholesten-3b,25-diol, and cholesterol showed that both 5a-cholestan-3b-ol-6-one and 5-cholesten-3b,25-diol were able to partially recover the wild type $T_m$, indicating their utility as pharmacological chaperones. To confirm the direct interaction with cryAB in a distinct experimental platform, biolayer interferometry (described in Example 1) was used to determine that 5-cholesten-3b,25-diol binds to R120G cryAB with a $K_D$ of 10.1±4.4 µM. Measuring affinity for the test protein by biolayer interferometry (Octet Red) allows for the identification of false positives. Briefly, biotinylated cryAB is immobilized to streptavidin-coated pins and equilibrium association data across a hundred-fold concentration range is analyzed to generate the apparent $K_D$. To control for nonspecific binding, the response of a biocytin-blocked pin is subtracted from each sensorgram.

Taken together, the results above demonstrate that compounds of Formula I function as pharmacological chaperones for R120G cryAB in vitro and bind with high affinity. Moreover, the results indicate that the disclosed DSF methods represent a robust high-throughput screening system for identifying novel pharmacological chaperones for non-enzymes.

Example 3

This Example demonstrates that the compounds identified in Example 1 suppress amyloid formation. Significantly, the compounds are also able to reverse amyloid formation.

The DSF studies suggested that sterols suppress R120G cryAB amyloid formation. To test this idea, R120G cryAB (15 µM) was treated with 5-cholesten-3b,25-diol or cholesterol (100 µM) and its ability to aggregate was measured by electron microscopy. These studies confirmed that 5-cholesten-3b,25-diol, but not cholesterol or the solvent control, dramatically suppressed amyloid formation. Visual inspection of the solutions supported this conclusion, because only 5-cholesten-3b,25-diol reduced the opacity of the R120G cryAB mixture. Moreover, 5-cholesten-3b,25-diol also reversed the aggregation of pre-formed R120G cryAB amyloids, suggesting that it shifts the equilibrium towards non-amyloid structures.

To explore the mechanism of action of 5-cholesten-3b, 25-diol, the binding site on R120G cryAB was explored by $^{15}$N HSQC NMR, and analysis of the resulting chemical shifts suggested that it binds an exposed face of the conserved crystallin domain. Specifically, 5-cholesten-3b,25-diol binds a groove across the cryAB dimer interface and makes contacts with residues near R120 and D109.

The above results support a model in which the sterol stabilizes the sHSP and reduces amyloid formation.

Example 4

This Example demonstrates that compounds identified herein reverse the cataract phenotype in vivo.

The R120G cryAB knock-in mouse is a clinically-acceptable model of aging-associated and hereditary cataract. The animal model develops severe cataracts within 20 weeks (Andley et al., *PLoS One* 6, e17671 (2011)). Excised eyes from these mice were treated with 5-cholesten-3b,25-diol (100 μM) or a saline control. 5-cholesten-3b,25-diol treatment significantly reduced the aggregation of cryAB and improved cryAB solubility.

5-cholesten-3b,25-diol was then formulated in a saline-cyclodextrin solution (5 mM cyclodextran; 5 mM 5-cholesten-3b,25-diol) and delivered by eye dropper three times a week for two weeks to live animals (n=15). cryAB solubility and lens transparency were determined by measuring slit lens illumination in live animals and by gel permeation chromatography/light scattering from lens homogenates. This treatment significantly improved cryAB solubility, improved lens transparency and rescued cataract phenotypes in 10/15 treated R120G cryAB knock-in mice. Thus, 5-cholesten-3b,25-diol, and more generally, a compound of formula I, is a promising therapeutic for the treatment of cataract. More broadly, these studies suggest that DSF-based HTS campaigns can be used to identify pharmacological chaperones for non-enzymes, such as cryAB.

Example 5

This Example demonstrates that compounds identified herein increase levels of soluble α-crystallin in the eye.

5-cholesten-3b,25-diol formulated in a saline-cyclodextrin solution (5 mM cyclodextran; 5 mM 5-cholesten-3b,25-diol) was delivered by eye dropper three times a week for two weeks to live mice (n=15). Gel filtration analysis of α-crystallin solubility was conducted by processing samples as previously described by Andley et al. (*PLoS ONE*, 6:3, 1-13 (2011)). Briefly, degree of aggregation of α-crystallin was determined using gel permeation chromatography (GPC) with light scattering and refractive index (RI) measurements. All data were analyzed using SAS version 9.3 (SAS Institute; Cary, N.C.). To control for differences in assay sensitivity among animals, the area under the curve for α-crystallin in the drug treated eye was compared to the area under the curve generated from the fellow untreated eye and expressed as "percent" difference in area using the untreated eye as the denominator. The percent difference between treated and untreated eyes was compared using the Wilcoxon signed rank test for the null hypothesis of no difference. The association between age and percent difference was calculated using the Spearman rank correlation coefficient. Non-parametric statistical models were used to protect from departures from normality.

The area under the curve of α-crystallin was found to be statistically significantly higher in the drug treated eyes versus the fellow untreated eyes (n=17, mean percent difference=381.2±974.6, median=63.3, Wilcoxon signed rank p-value=0.001). Older mice demonstrated a higher percentage increase in α-crystallin in treated eyes relative to untreated eyes (Spearman rank correlation=0.44, p=0.075). The data in Table 1 show a noticeable increase in median percent difference when the age is greater than 200 days.

| | | Age (days) | | | | | | |
|---|---|---|---|---|---|---|---|---|
| | | 66 | 79 | 184 | 192 | 200 | 266 | All |
| Percent differ- | N | 3 | 1 | 2 | 3 | 4 | 4 | 17 |
| | Mean | 177.2 | 98.1 | 61.4 | 22.7 | 38.7 | 1376.3 | 381.2 |

-continued

| | | Age (days) | | | | | | |
|---|---|---|---|---|---|---|---|---|
| | | 66 | 79 | 184 | 192 | 200 | 266 | All |
| ence in area between untreated and treated eyes | Standard Deviation | 347.9 | — | 2.7 | 68.4 | 25.9 | 1799.8 | 974.6 |
| | Median | −20.2 | 98.1 | 61.4 | 55.8 | 31.8 | 679.0 | 63.3 |

The data reveal that a compound of formula I, 5-cholesten-3b,25-diol, significantly increased solubility of α-crystallin in vivo, particularly in aged subjects, thereby targeting an underlying mechanism of cataract formation.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosed subject matter have been illustrated and described, it would be apparent to those skilled in the art that various other changes and modifications can be made without departing from the spirit and scope of the subject matter claimed. It is therefore intended to cover in the appended claims all such changes and modifications.

What is claimed is:

1. A method of reducing aggregation of an α-crystallin protein by at least 5% in an eye of a subject in need thereof, wherein the subject has age-related cataract, diabetic cataract, a hereditary form of cataract, a cataract associated with surgery, a cataract resulting from exposure to radiation, a cataract resulting from a genetic illness, a cataract resulting from an infection, or a cataract resulting from medication, the method comprising administering to an eye of the subject in need thereof an effective amount of a composition comprising a compound represented by the formula:

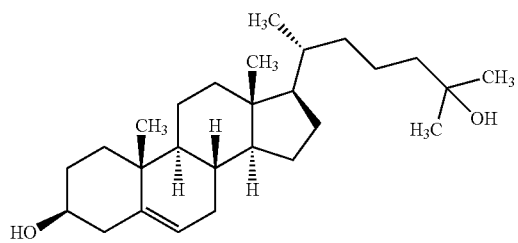

or a pharmaceutically acceptable salt thereof.

* * * * *